(12) United States Patent
Ames et al.

(10) Patent No.: US 6,991,728 B2
(45) Date of Patent: Jan. 31, 2006

(54) APPARATUS AND METHOD FOR THE TREATMENT OF WASTE

(75) Inventors: Roy Victor Ames, Hawthorne (AU); Matthew John Etherington, Maraylya (AU); Nicholas Michael Czeperko, Rochedale (AU); Ian Joseph Ugarte, Berowra Waters (AU)

(73) Assignee: Aqua Clarus Holdings Pty Ltd, (AU)

( * ) Notice: Subject to any disclaimer, the term of this patent is extended or adjusted under 35 U.S.C. 154(b) by 0 days.

(21) Appl. No.: 10/705,734

(22) Filed: Nov. 10, 2003

(65) Prior Publication Data

US 2005/0006304 A1    Jan. 13, 2005

Related U.S. Application Data

(63) Continuation-in-part of application No. PCT/AU02/00559, filed on May 3, 2002.

(30) Foreign Application Priority Data

May 10, 2001    (AU)    .................................... PR4902

(51) Int. Cl.
  *B01D 43/00*    (2006.01)
  *C02F 3/32*    (2006.01)
  *C02F 3/04*    (2006.01)
  *E03F 5/14*    (2006.01)

(52) U.S. Cl. ...................... 210/602; 210/617; 210/143; 210/151; 210/259

(58) Field of Classification Search ................ 210/602, 210/616, 617, 620, 138, 259, 260, 150, 151, 210/143
See application file for complete search history.

(56) References Cited

U.S. PATENT DOCUMENTS

| | | | | |
|---|---|---|---|---|
| 3,635,816 A | * | 1/1972 | Golub | 210/602 |
| 4,085,040 A | * | 4/1978 | Egan | 209/244 |
| 4,113,626 A | * | 9/1978 | Detcher | 210/409 |
| 4,519,902 A | * | 5/1985 | Kinder | 209/234 |
| 5,078,882 A | * | 1/1992 | Northrop | 210/602 |
| 5,137,625 A | * | 8/1992 | Wolverton | 210/195.1 |

(Continued)

FOREIGN PATENT DOCUMENTS

GB    2077712    * 12/1981

(Continued)

OTHER PUBLICATIONS

"International Search Report for PCT Application No. PCT/AU02/00559", (Jul. 9, 2002), 1 pg.

*Primary Examiner*—Fred G. Prince
(74) *Attorney, Agent, or Firm*—Schwegman, Lundberg, Woessner & Kluth, P.A.

(57) ABSTRACT

The present invention relates to a treatment system for treating primary waste onsite. The treatment system includes a separation cone which separates the solid waste from the liquid waste and the different wastes are subsequently treated separately. The solid wastes are subject to aerobic decomposition by worms and other suitable organisms while liquid wastes are filtered through alternate layers of coarse and fine filter media. The resulting treated liquid can be recirculated or pumped out of the system for other purposes or further treatment. The treatment system is designed as a compact modular system and maybe used for the treatment of domestic human waste.

42 Claims, 12 Drawing Sheets

U.S. PATENT DOCUMENTS

| | | |
|---|---|---|
| 5,633,163 A | 5/1997 | Cameron |
| 5,919,366 A | 7/1999 | Cameron |
| 5,976,374 A | 11/1999 | Cameron |
| 6,126,827 A * | 10/2000 | Johnson et al. ............. 210/602 |
| 6,238,563 B1 | 5/2001 | Carroll, II et al. |
| 2001/0045392 A1 | 11/2001 | Gray et al. |

FOREIGN PATENT DOCUMENTS

| | | |
|---|---|---|
| RU | 2022616 C1 | 11/1994 |
| RU | 2097150 C1 | 11/1997 |
| WO | WO-99/01385 A1 | 1/1999 |
| WO | WO-02/46127 A2 | 6/2002 |

* cited by examiner

TOP TRAY 15

SECOND TRAY 16

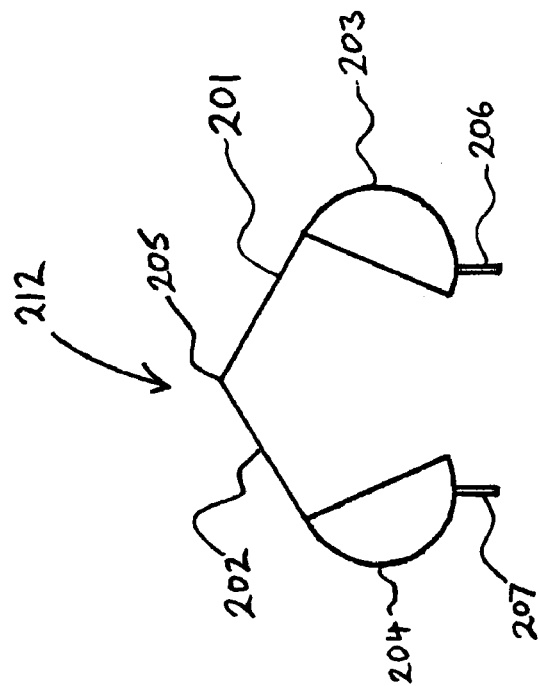
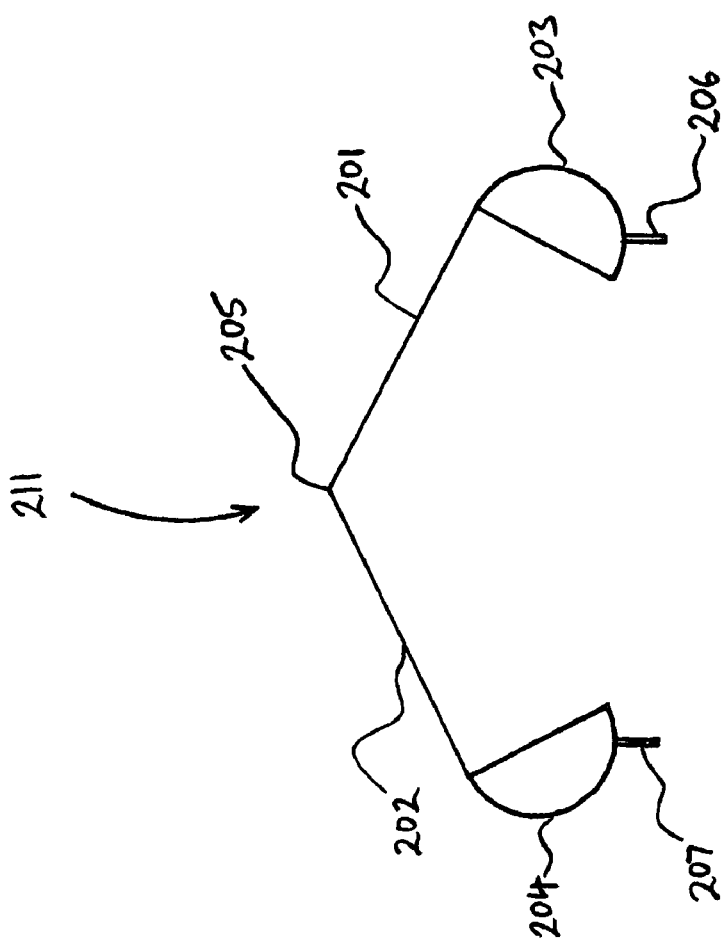
FIGURE 13(b)
FIGURE 13(a)

APPARATUS AND METHOD FOR THE TREATMENT OF WASTE

RELATED APPLICATIONS

This application is a continuation-in-part U.S. National Stage filing from International Application No. PCT/AU02/00559 filed May 3, 2002 and published in English as WO 02/089957 on Nov. 14, 2002, which claimed priority from Australian Application SN PR4902 filed May 10, 2001, which applications and publication are incorporated herein by reference.

FIELD OF INVENTION

The present invention relates to the treatment of waste products including solid and liquid domestic and human waste. The invention has particular but not exclusive application for onsite treatment of domestic sewerage.

PRIOR ART

The managing and treatment of domestic sewerage and other waste is a growing problem facing cities and other populated areas. In lightly populated areas there is often a lack of appropriate sewerage facilities. If the sewerage is not appropriately treated, it can contaminate water supplies and subsequently affect the health of the inhabitants.

One approach to the problem has been the development of onsite treatment systems that minimise the amount of waste leaving a property or dwelling. In general however many onsite treatment systems have relatively high operating costs and require regular servicing.

A large number of onsite treatment systems for sewerage such as a septic tank involve an anaerobic digestion stage. Odours produced from anaerobic digestion can cause problems. Furthermore the initially treated sewerage requires more extensive subsequent treatment before it can be discharged. Septic systems also require periodic pumping out of the residual sludge. In addition septic systems are becoming less popular with regulatory authorities because of their potentially harmful effect on the environment. Many alternative systems developed to replace septic systems have a range of problems including reliability.

With aerobic treatment systems the sewerage is aerated usually with the use of blowers or other mechanical means of aeration. The blowers and other mechanical means require maintenance and their use increases operating costs. Several aerobic treatment systems have been developed. An aerobic treatment system described in AU652879 involves passing the waste through a bed of suitable filtration material containing a population of composting worms or microbes. The filtration bed of this system is relatively large in area and all liquids and solids pass through the bed. The mixture of liquid and solid waste serves as the substrate for the microbes and worms. The solids either remain in the device causing problems at a later stage or have to be manually removed from the bed. The effluent from this process is of relatively poor quality.

SUMMARY OF THE INVENTION

The basis of the present invention was the development of a separating means to separate solid and liquid waste for separate treatment. The separating means has a geometrical shape that allows substantially all of the solid waste to fall off an outer surface and the majority of the liquid waste to flow on the surface and into a liquid collection means. The shape of the separating means preferably allows liquid waste to flow along the outer surface by means of surface tension.

In one aspect the present invention provides a separating means for separating liquid and solid waste, wherein the separating means has a substantially non porous inclined surface with a curved lower outer edge to allow solid waste to fall off the separating means while liquid waste moves around the curved lower outer edge.

The outer surface is preferably an inclined surface with a curved lower outer edge. The degree of inclination of the outer surface preferably enables the separating means to be substantially self cleaning. The preferable angle of inclination of the outer surface is an angle that facilitates the downward movement of particulate and liquid waste. The angle of inclination is preferably between 10 and 40 degrees, more preferably between 20 and 30 degrees from the horizontal axis. The lower curved outer edge is preferably a convex curved surface curving inwardly and under the inclined surface. The curve of the outer edge preferably facilitates the falling off of particulate waste but allows liquid waste to move around the outer edge.

The separating means may be an inclined wall adjacent a waste discharge outlet and having a curved lower edge that extends, at least in part, substantially horizontally under the inclined wall. Hence, the separating means may be a closed structure having a substantially horizontal base or it may be an open structure having a substantially horizontal inward projection from its side wall(s).

The separating may have one inclined surface. For example, the separating means may be substantially in the shape of a cone or a hemisphere. Alternatively, the separating means may have a plurality of inclined surfaces. For example, the separating means may be substantially in the shape of a pyramid or prismoid. Any of these geometric shapes may be either with or without a base, as mentioned above.

The separating means preferably substantially overhangs the liquid collection means so that liquid flows around the curved lower edge of the outer surface and drips into the liquid collection means while particulate matter falls off the outer surface as the matter moves around the curved lower edge. The liquid collection means may be in the form of, for example, a tray or a chamber.

Preferably, the separating means includes a flange on its lower edge for directing liquid waste into the liquid collection means. Preferably, the flange extends downwardly from a substantially horizontal part of the curved lower edge.

The inclined surface(s) is substantially non porous. By "substantially non porous", it is contemplated that in some forms of the invention, the surface may have a degree of porosity such that some liquid can pass through directly to the liquid collection means. Notwithstanding, the majority of liquid will still be separated by moving around the curved lower outer edge. However, the term "substantially non porous" may also mean, in some forms, that the inclined surface is completely non porous.

In a preferred embodiment the separating means is a substantially non-porous separating cone locatable with its apex uppermost and with the apex adjacent to a waste discharge and a convex lower curved surface that turns inward to form the base wall.

The separating cone is preferably adaptable to be retrofitted to an existing treatment system.

In another particularly preferred embodiment, the separating means comprises two substantially non porous inclined surfaces, each having curved lower outer longitudinal edges, and sharing a common upper edge, which defines a top edge of the separating means. A separating means in this form has the advantage of simpler and cheaper construction.

Preferably, each of the inclined surfaces is elongate and shares a common longitudinal upper edge. An advantage of elongate surfaces is that the surface area of the separating means is increased without increasing the overall height. With a greater surface area, greater separating efficiency can be achieved with a correspondingly increased capacity for receiving waste material.

Preferably, the separating means described above further comprises a longitudinal flange along each of the curved lower longitudinal outer edges, the longitudinal flanges being positioned for directing liquid waste into a liquid collection means, such as a tray beneath the flanges.

Preferably, the separating means described above has a first end locatable adjacent a waste discharge outlet and a second end locatable distal to the waste discharge outlet. Hence, waste from the discharge outlet flows longitudinally along the separating means while simultaneously flowing down from the top edge to the lower outer longitudinal edges, thereby increasing separating efficiency by increasing the surface area exposed to the waste mixture.

Preferably, each of the inclined surfaces is tapered towards the second end of the separating means (which is distal to the waste discharge outlet), such that the second end is smaller in cross-section than the first. An advantage of this configuration is that it reduces the surface area of the separating means in areas where the velocity of waste is relatively low. This reduces the tendency for solid build up on the separating means.

Preferably, the separating means has a height dimension of less than 200 mm. Typically, separators known in the prior art require a relatively large height dimension, which impacts on the overall compactness of systems containing such separators. With the novel separating means of the present invention, a relatively small height dimension is achievable whilst maintaining excellent separating efficiency.

In another aspect, the present invention provides a waste treatment system including a decomposition chamber having an inlet, said decomposition comprising:

a separating means as described above; and a solid waste treatment means and a liquid waste treatment means.

The separation means, solid waste treatment means and liquid waste treatment means are preferably arranged in relative close proximity with each other to provide a compact treatment apparatus.

The decomposition chamber is preferably circular in cross section to provide maximum usage of space within the chamber and house the components in a compact manner.

The treatment system may be modular with a plurality of units arranged to handle larger amounts of waste. Alternatively each unit may be increased in size to cater for larger amounts of waste.

The waste chamber inlet provides a passage for waste from a domestic source or the like to enter the decomposition chamber. The waste inlet is preferably positioned above the separation means.

The separating means is preferably in the form of either:

(a) a substantially non-porous separating cone, wherein an apex of said cone is located adjacent a waste discharge outlet; or (b) two elongate substantially non porous inclined surfaces, each having curved lower outer longitudinal edges, and sharing a common upper longitudinal edge which defines a substantially horizontal top edge of the separating means, wherein one end of the separating means is located adjacent a waste discharge outlet.

The waste inlet and/or waste discharge outlet preferably has a skirt or baffle. The skirt or baffle preferably extends about the periphery of the inlet opening. The skirt or baffle preferably serves to restrict the flow of waste into the chamber and ensure relatively even distribution of the waste over separating means. The skirt or baffle may be formed from flexible material such as vertically positioned plastic strips.

Solid waste that falls off the separating means preferably is treated by the solid waste treatment means. The solid waste treatment means is preferably located below the separating means. Preferably a minimal amount of liquid is also treated with the solid waste by the solid waste treatment means. Preferably one to twenty percent of liquid waste and more preferably less than ten percent of liquid waste is treated by the solid waste treatment means. In one preferred embodiment two percent is treated by solid waste treatment means.

The solid waste treatment means preferably includes one or more support mesh screens substantially horizontal, the support mesh screen(s) being positioned for receiving solid waste, preferably below the separating means. The support mesh screens are preferably disposed one above the other and are separated by substantially equal distances. The upper screen preferably has wider apertures than the adjacent screen below. In one preferred embodiment the solid waste treatment means includes a series of support screens.

An uppermost screen may include a plurality of baffles for breaking up the solid waste and exposing greater surface area of the solid to the air to avoid decomposition. The baffles may be in the form of, for example, mushroom-shaped projections or nodules. A lowermost screen may be inclined to direct decomposed particulate solids towards a solids pump well.

In one embodiment, there are three screens with an upper screen preferably formed from 25 mm woven mesh material, while a middle screen and lower screen preferably formed from 13 mm and 5 mm woven mesh material respectively. In another embodiment there are two screens with an upper screen being 10 mm and a lower screen being 5 mm woven mesh.

Each support screen preferably has one or more sections where the gauge of the apertures are smaller so that the solid waste is retained until it is decomposed to a size that will pass through to the screen. The sections with the smaller gauge apertures are offset relative to corresponding sections in the adjacent support screens. Making the sections with the smaller gauge apertures offset relative to corresponding sections in adjacent screens prevents solid waste from moving to the lower screen without undergoing decomposition on one of the upper support screens.

The support screens preferably support a population of worms and other suitable organisms preferably introduced into the chamber during installation. Worms and other suitable organisms are introduced to consume the waste, reduce the size of the particles and maintain aeration in the decomposing waste.

The worms and other suitable organisms may be introduced as part of an inoculum chamber mounted within the decomposition chamber whereby the organisms have access to the support screens. Alternatively the worms are added directly to the trays.

The support screens and the inoculum chamber are preferably mounted within a solids decomposition compartment. The porous solids decomposition compartment has a cylindrically-shaped side wall that preferably extends about the separating cone and downwardly below the lower support screen and a base wall.

The solids pump well is substantially centrally located in the base wall of the porous solids decomposition compartment. Preferably one or more drainage holes in a wall encompassing the solids pump well provides communication between the solids decomposition compartment and the solids pump well. On the base wall of the solids decomposition compartment there is preferably a plurality of drainage cells which serve to store and passage liquid to the solids pump well.

There may also be a fine mesh drainage filter that is located on the drainage cells and directs decomposed small particles to the solids pump well.

In an alternative embodiment, an inclined screen (rather than drainage cells) serves to collect the majority of small particulate solids. These small solids build up and fall towards the solids pump well. Directly below the screen is an inclined nonporous surface that collects any liquid draining through the inclined screen together with any small particulate solids that pass through the screen. These solids are washed by the liquid towards the solids pump well.

The solids pump well preferably houses a pump means that pumps out the small particles and liquid. The pump means may be activated on a predetermined regular basis or when liquid reach a predetermined height within the solids pump well.

The particles and liquid are preferably pumped to a storage means. The liquid pumped from the solids pump well may be further processed as described below. The storage means is preferably disposed near the top of the chamber and is accessible to allow removal of the stored solids. In one embodiment the solids and liquid is pumped to a vegetation cell or an external trench.

Decomposition of the solid waste preferably occurs under aerobic conditions.

The solids decomposition compartment is preferably passively aerated. The solids decomposition compartment is preferably aerated as a result of one or more vents in the decomposition chamber.

A major portion of the liquid waste preferably runs down the non-porous outer surface of the separating means, follows the curved surface inwardly and drips into a liquid collection means. In a preferred form, the liquid collection means is a collection chamber or collection tray located under the separating means. The separation means preferably overhangs the collection chamber thereby substantially avoiding the collection of solids waste.

A major portion of the liquid waste separated from the waste stream by the separating means is preferably treated by the liquid waste treatment means. The portion of liquid waste treated by the liquid waste treatment means is preferably ninety percent and more, preferably ninety-five percent or more.

Liquid waste is preferably collected from the separating means in a liquid collection means and then treated by the liquid waste treatment means.

The liquid waste treatment means preferably includes one or more layers of trickle bed media. Preferably the liquid waste treatment means includes a plurality of layers with alternating relatively coarse trickle bed media and relatively fine trickle bed media. The relatively coarse trickle bed media may include particularized agricultural pipe whereas relatively fine trickle bed media may include peat moss.

Each of the layers of relatively coarse trickle bed media are preferably well ventilated. The layers of relatively fine trickle bed media are preferably not well ventilated and act as anaerobic zones. The liquid waste passing through the trickle beds preferably serves as a substrate for colonized bacteria populations to reduce the BOD (Biochemical Oxygen Demand) of the liquid. Some of the nitrogen may also be removed as a result of nitrification/denitrification in the alternate fine/coarse trickle bed layers.

In a preferred embodiment, the liquid separated by the separating means is introduced about midway between the trickle bed layers.

In a preferred embodiment, the trickle bed layers form annularly about the solid waste treatment means. The wall of the solid decomposition compartment may in one or more areas be porous to allow ventilation of trickle bed layers. By having one or more porous areas, any particulate solids that accumulate within the trickle bed layers may be decomposed by worms and other suitable organisms passing through into these beds. The side wall of the solids decomposition compartment is preferably porous. Liquid passing through the trickle bed layers in a sideways direction reaches the sidewall and flows downward and does not pass through into the solids decomposition compartment (possibly by means of surface tension)

Worms and other organisms pass through the porous side wall.

There is preferably a liquid pump well where liquid that has permeated through the trickle bed is collected and stored and pumped for recirculation in the liquid waste treatment means, discharged to an external trench or vegetation cell, or used for subsoil irrigation. The liquid is pumped by suitable pump means and preferably controlled by a float switch and controller which activates the pump means at set times or when the liquid level in the pump well reaches a predetermined level.

In one embodiment, the controller may be activated and in communication with a remotely located transmitter means such as by a suitably programmed telephone or computer, for activating and monitoring the performance of the system offsite.

The liquid and solid treated waste may be further processed to produce products that can be used in other applications. The further processing of the treated waste may be formed to a standard required for the product's application.

For example, it has been found that simple pressure filtration is capable of upgrading the liquid from the first treatment apparatus to a liquid suitable for surface irrigation after a disinfection step. Also the treated waste liquid may undergo additional processing for recycling back to the household for non-potable uses or even more extensive processing to produce drinkable water. For example the treated waste liquid may be further processed by any one or combination of treatments including passage through a sand and/or carbon and/or membrane filter, an ozone treatment system to remove colour and precipitate solids, and disinfection by any suitable means.

In another embodiment, the waste treatment system may include a vegetation cell for supporting a plant, wherein, in use, treated solid waste and/or treated liquid waste is discharged to the vegetation cell. The vegetation cell supplies nutrients and/or moisture to a plant growing medium.

The present invention also provides a self-contained waste treatment system, which does not require human intervention for removal of treated waste, comprising:

a decomposition chamber having a waste chamber inlet, said decomposition chamber housing a separation means, a solid waste treatment means and a liquid waste treatment means; and a vegetation cell for supporting a plant, wherein, in use, treated solid waste and, optionally, treated liquid waste is discharged to the vegetation cell.

There is also provided a self-contained process for treating waste, which does not require human intervention for removal of treated waste, said process comprising the steps of:

(a) separating liquid and solid waste using a separating means;

(b) treating the separated liquid waste in a liquid waste treatment means;

(c) treating the separated solid waste in a solid waste treatment means;

(d) optionally further treating the liquid waste; and (e) discharging the treated solid waste and, optionally, the treated liquid waste to a vegetation cell.

All aspects of the waste treatment system described herein may also be included in the self-contained waste treatment system and process above.

BRIEF DESCRIPTION OF THE DRAWINGS

In order that the present invention be more readily understood and put into practical effect, reference will now be made to the accompanying drawings wherein:

FIG. 13(*a*) is a cross-sectional view of a first end of the separating means of FIG. 12.

FIG. 13(*b*) is a cross-sectional view of a second end of the separating means of FIG. 12.

DETAILED DESCRIPTION OF THE PREFERRED EMBODIMENTS

Figure 1:
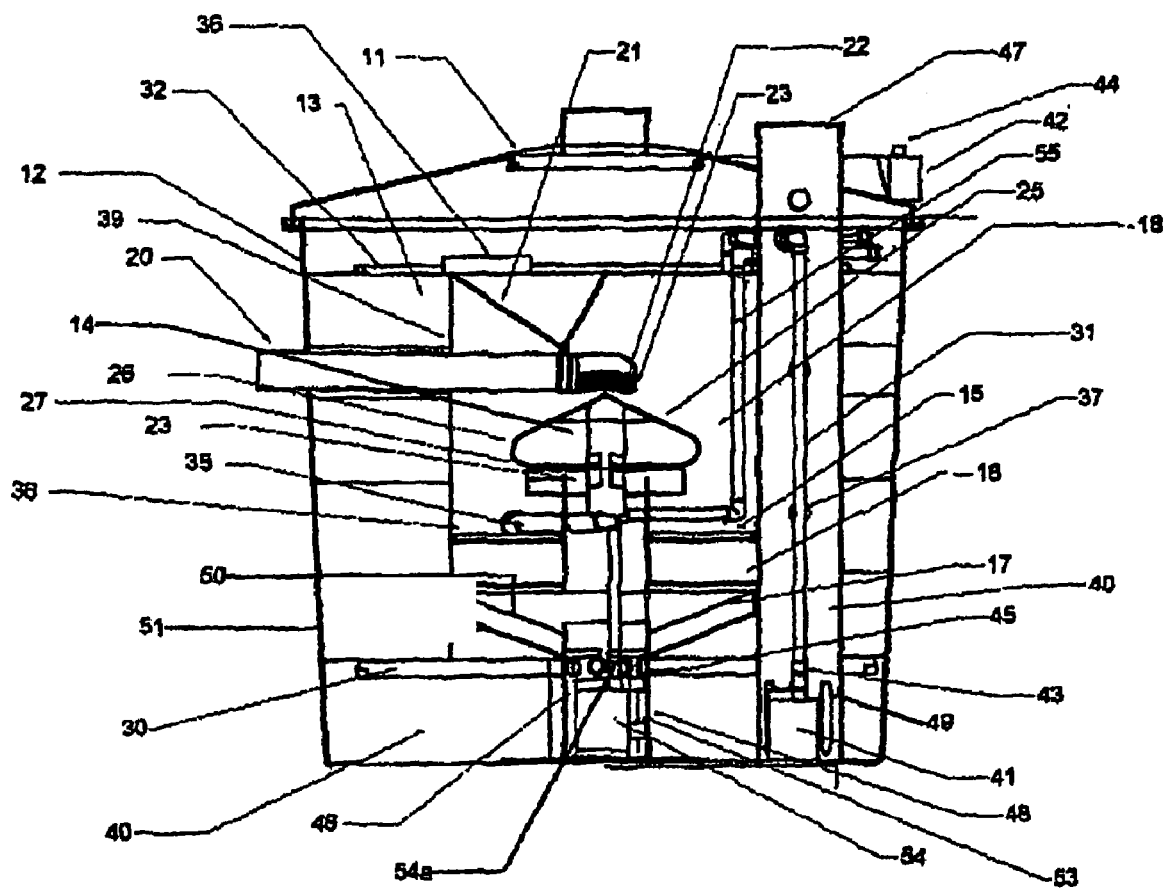
FIG. 1 is a vertical cross-sectional view of a first embodiment of the waste treatment apparatus according to the present invention.
Figure 2:
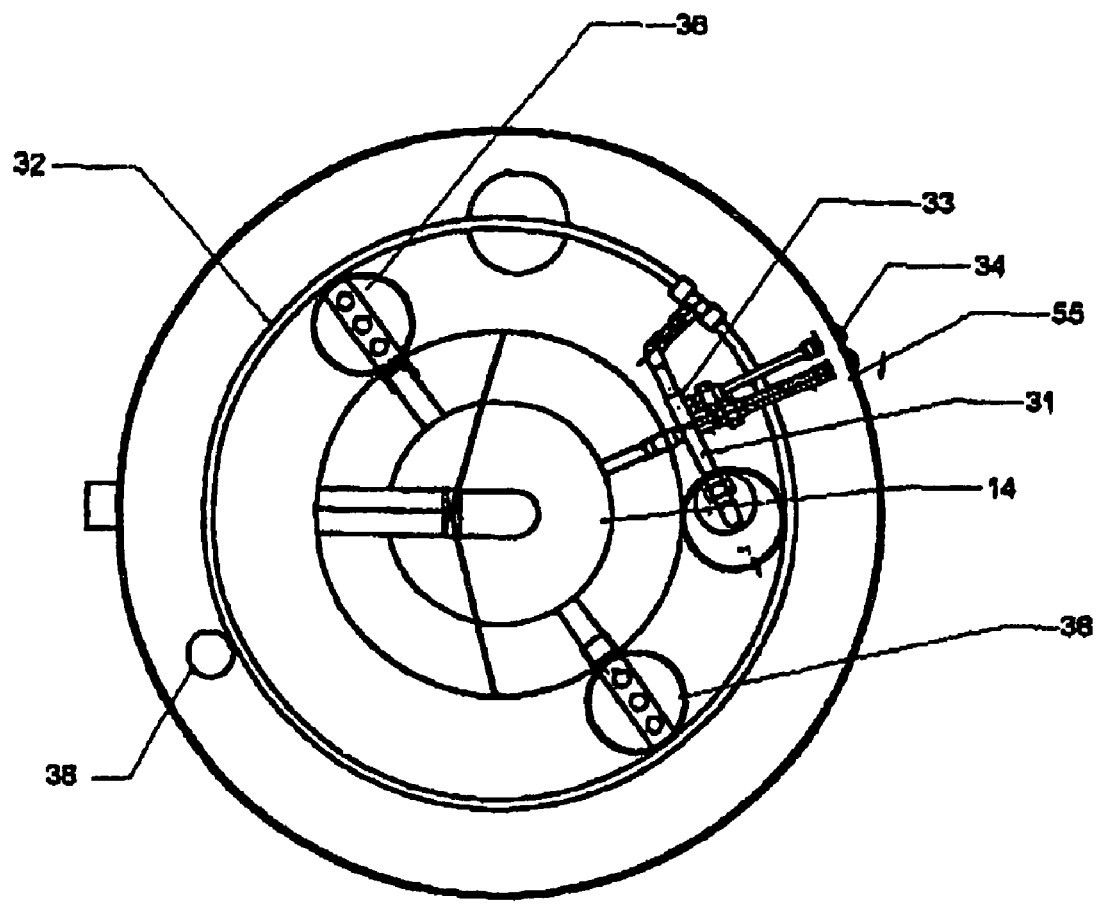
FIG. 2 is an upper horizontal cross sectional view of the apparatus of FIG. 1.
Figure 3:
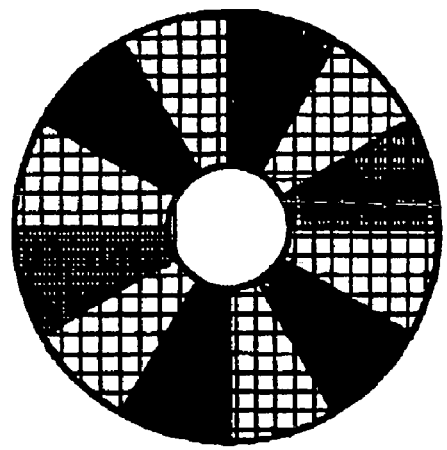
FIG. 3 is a plan view of the support screens of the apparatus of FIG. 1.
Figure 3:
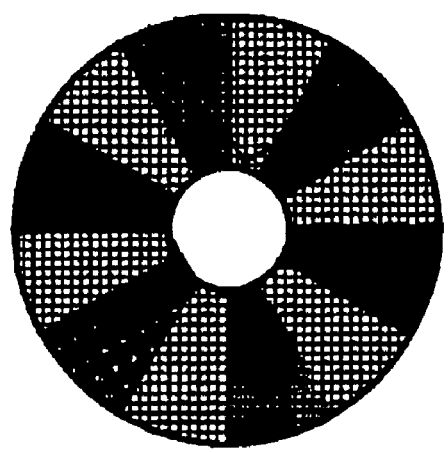
Figure 4:
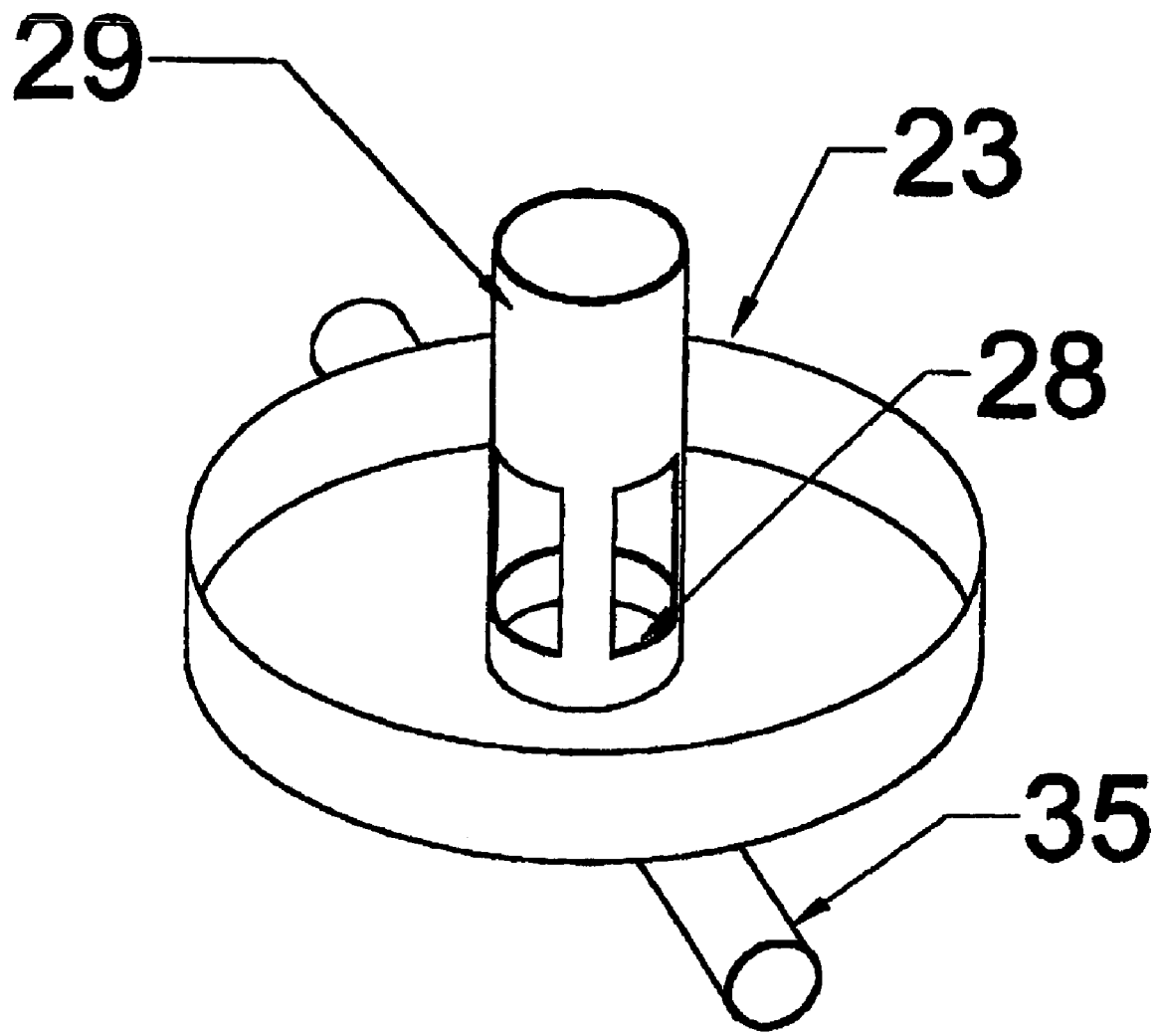
FIG. 4 is a perspective view of the collection well of the apparatus of FIG. 1.
Figure 5:
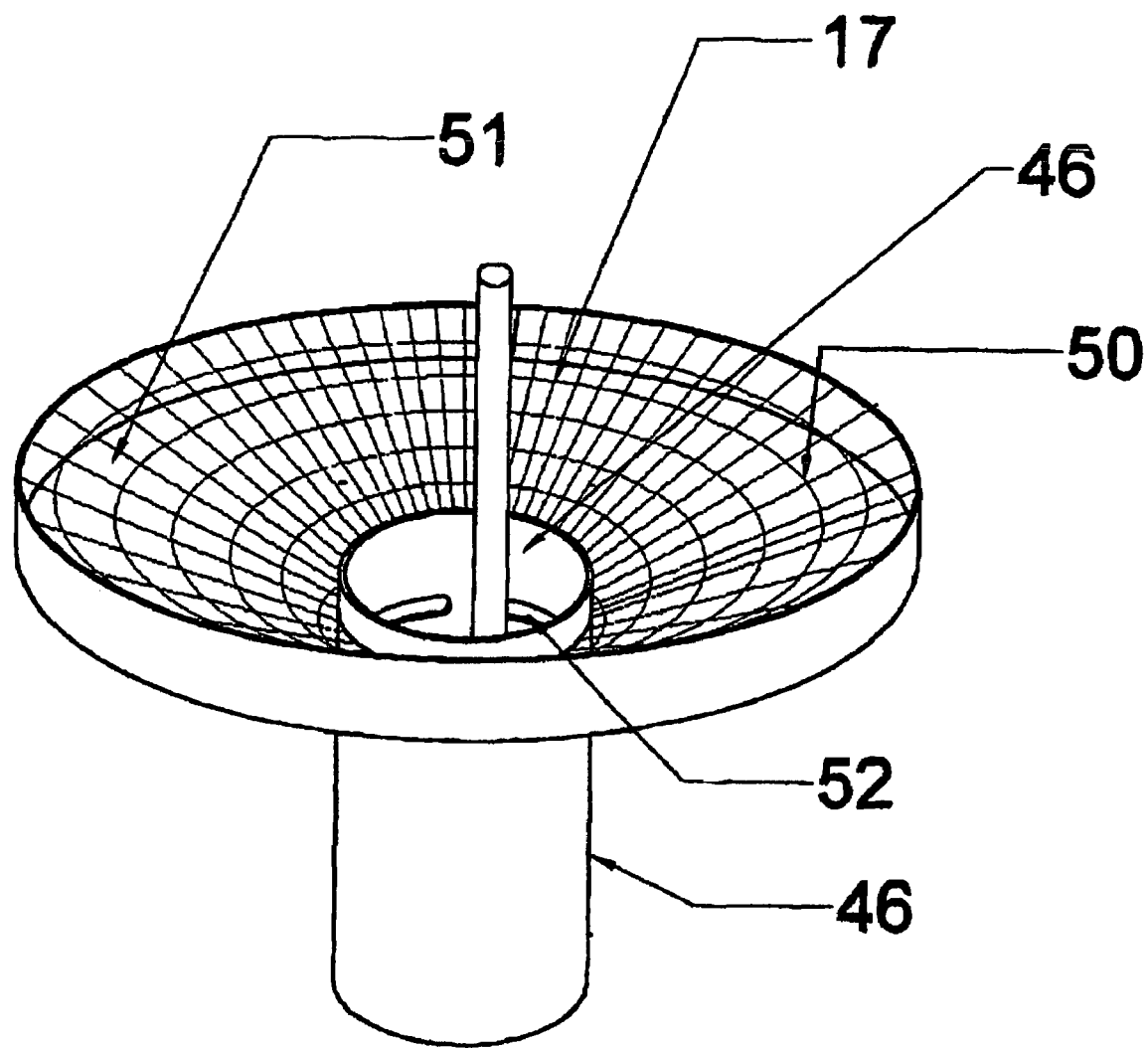
FIG. 5 is a perspective view of the inclined screen of the apparatus of FIG. 1.

Two embodiments of the apparatus for the treatment of wastewater generated from a typical domestic house are shown in FIGS. 1 to 5 (first embodiment) and 8 to 10 (second embodiment).

First Preferred Embodiment

With reference to FIGS. 1 to 5 there is shown a waste treatment apparatus 11. The waste treatment apparatus 11 has an outer housing 12 that surrounds a substantially ring shaped trickle bed 13, a centrally located separating cone 14, two solids decomposition trays 15 and 16 located below the separating cone 14 and a substantially concave screen 17.

Waste is introduced into housing 12 through waste inlet pipe 20 which is positioned by supports 21 so that the opening 22 is above the separating cone 14.

The opening 22 has a baffle 23 that directs waste towards the apex of the cone 14.

The cone 14 is non-porous and shaped so that waste runs downwardly from the apex along inclined surface 25. The inclined surface 25 has an approximate 25 degree angle with respect to the horizontal axis. The cone diameter in the preferred embodiment is 560 mm while the radius of the lower curved surface is 46 mm.

From the inclined surface 25 a major portion of the liquid waste moves around the lower curved surface 26 of the cone 14, along the base wall 27 of the cone 14 and drips into the collection well 23. The lower curved surface 26 overhangs the collection well 23 so to avoid solid waste particulates from falling into the collection well 23. The movement of the liquid waste around the lower curved surface 26 is possibly due to surface tension. In contrast solids waste falls off the separating cone 14 as it moves around the lower curved surface 26. Smaller solids waste particulates may move further around the lower curved surface than larger solids waste particles. The majority of solids waste falls off into the solids decomposition tray 15 while very small solids waste particulates may move along the base wall 27 with the liquid waste and fall into the collection well 23.

The liquid waste flows over baffle 28 and then piped from the collection well 23 along pipes 35 into distribution wells 36 and introduced into a coarse media layer in the lower part of the trickle bed 13. Baffle 28 forms part of the support 29 for mounting the separating cone 14. The distribution wells 36 are substantially on opposite sides of the trickle bed 13. The trickle bed 13 consists of alternate layers of fine and coarse filter media. In one form there is six alternate layers of coarse (crumbed or chopped agriculture pipe) filter and fine (particulates of 3 to 25 mm) filter. The coarse filter layers are aerated through outlets 37 in vent 38 and pump-well 47. Liquid waste passes though the trickle bed media while undergoing decomposition and BOD reduction. Liquid is substantially prevented from passing from the trickle bed 13 to the central cavity 18 by barrier 39. The barrier 39 is made of porous material allowing aeration of the trickle bed media and retaining the integrity of the trickle bed 13. Liquid passing through the trickle bed 13 and in contact with the porous barrier 39 flows down the trickle bed-barrier surface and does not pass through to the central cavity 18.

The trickle bed 13 is supported on a series of drain pipe sections 30 formed in a spoked wheel arrangement. The drain pipe sections 30 pass through a central pump well housing 48.

Liquid after passing through the trickle bed 13 accumulates in a collection chamber 40 and is recirculated by pump 41 in liquid pump well 47 to the top of the trickle bed 13. Liquid reaches pump 41 by passing through opening 49 which provides communication between the collection chamber 40 and the liquid pump well 47. The controller 42 activates liquid pump 41 and controls the recirculation time and the interval time.

The liquid is pumped by liquid pump 41 through circulation pipes 31 to distribution pipes 32 which have a series of apertures for reintroducing liquid to the trickle bed 13. The distribution pipes 32 substantially overlays the trickle bed 13 in a ring-like arrangement. In cases where no further treatment is required a small portion of the liquid is diverted at a T-junction 33 formed with circulation pipes 31.

Liquid is diverted through the T-junction 33 and diversion pipe 34 to the outside of the waste treatment apparatus 11 such as to an external trench. In cases where further treatment is required the liquid can be discharged from the treatment apparatus 11 through pipe 31 and a portion recirculated to distribution pipes 32 overlaying the trickle bed 13.

If the liquid pump 41 fails the liquid collects in the collection chamber 40 and the liquid pump well 47. At a preset level, a high level indicator 43 activates an alarm light 44 and liquid passes through slot 45 in the central pump well housing 48 into the central pump well 46 for removal.

Solid waste and a small amount of liquid falls into the solids decomposition tray 15. Worms and other organisms involved in the decomposition of solid waste are introduced onto trays 15,16 during installation and start up. The worms and other organisms consume the solid waste and reduce particle size. As particle size is reduced they fall through the mesh trays 15 and 16. Mesh tray 15 (approximately 10 mm gauge mesh) with six segments of finer mesh spaced equidistant around the tray 15. The finer mesh segments serve to retain the larger particles for further decomposition. Mesh tray 16 (approximately 5 mm gauge mesh) is immediately below tray 15. Biological decomposition with worms and other organisms continues on tray 16. Tray 16 also has finer mesh segments offset (approximately 30 degrees) to the finer mesh segments in tray 15. Both trays 15 and 16 are substantially horizontal.

Concave or dish shaped screen 17 has an inclined mesh surface 50 to direct small particles to the centre of the screen 17 so that they can enter the central pump well 46. Biological decomposition also occurs on screen 17. Screen 17 has a 2 mm mesh surface 50 which allows liquid and very fine particles to pass through to an inclined base wall 51. The liquid moves downwards and passes through the apertures 52 and into the central pump well 46. When the liquid moves downward it collects the very fine particles which also pass into the central pump well 46.

When material in the central pump well 46 accumulates above a set level, a float switch 53 activates central pump 54 and the material is transferred through a transfer pipe 55 out of the system to a vegetation cell 60. If central pump 54 fails to be activated, level alarm 54a and light alarm 44 is activated. If central pump 54 fails to be activated, material overflows through slot 45 and into the collection chamber 40. Material is then pumped away by liquid pump 41 through the circulation pipes 31 as discussed above. In this situation the material maybe directed out of the waste treatment apparatus 11 through the diversion pipe 34.

Where the treatment apparatus 11 is approximately 1800 mm in diameter and 1800 mm in height it may be used to treat the domestic waste for approximately 10 people (approximately 2000 litres per day).

Digestion of the liquid and solid waste proceeds largely aerobically because of aeration provided to all parts of the system through ventilation to the trickle bed 13 and solids decomposition trays 15,16, and screen 17 from a vented central cavity 18. The central cavity 18 is passively vented through vents 38 in the upper portion of the treatment apparatus 11.

Figure 6:
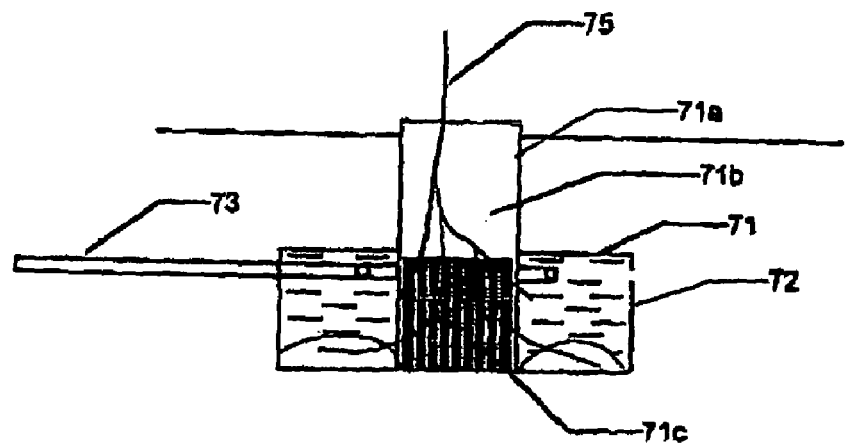
FIG. 6 is an elevation view of a vegetation cell.
Figure 7:
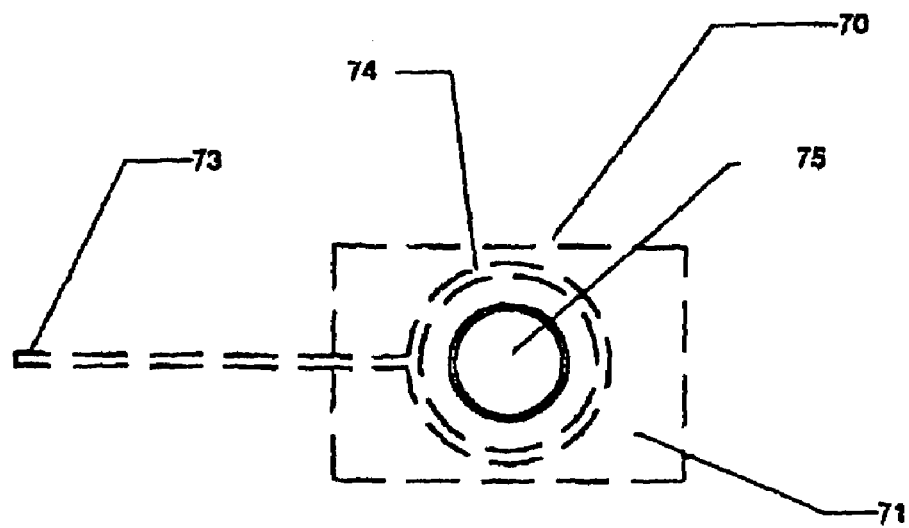
FIG. 7 is a plan view of the vegetation cell of FIG. 6.

With reference to FIGS. 6 and 7 there is shown a vegetation cell 70 which is a chamber 71 slotted at the side and end walls 72 but with no base wall. The top of the chamber 71 is buried 300 mm below ground level. There is a plant tube 71 a positioned within the vegetation cell 71 in which a suitable plant 75 may be grown.

The plant tube 71a contains suitable plant growing medium such as potting mix or gravel. The plant tube 71a has a sidewall 71b which has a lower porous portion 71c located within the vegetation cell 71. The porous portion 71c permits nutrients and moisture to pass through into the plant tube 71a. A discharge pipe 73 (which may correspond with discharge pipe 55) from the treatment system 11 enters the chamber 71 and serves to introduce treated liquid and solids. A distribution ring 74 connected from pipe 73 distributes liquid and solid around the chamber. The plant tube 71 a is centrally located within the distribution ring 74.

Figure 8:
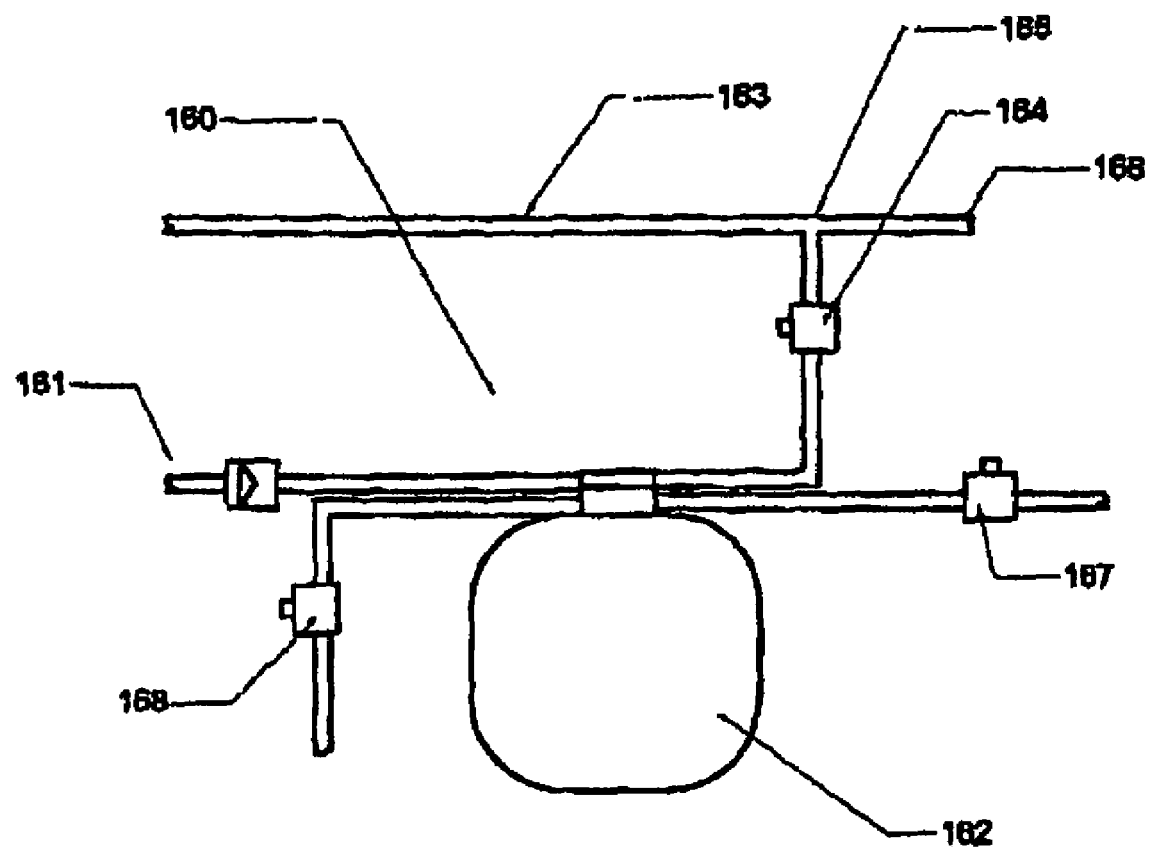
FIG. 8 is an elevation of a subsequent treatment process involving filtration.

In cases where further treatment is desirable one alternative system 160 is shown in FIG. 8. Liquid discharged through pipe 31 passes through a non-return valve 161 to a filter 162 containing sand or other filtering media. The liquid is then recirculated back to the distribution pipe 32 in the water treatment apparatus 11 through pipe 163, valve 164 and T-pipe 165. At approximately the same time, a small quantity of liquid is discharged for further treatment and/or disinfection through valve 164, T-pipe 165 and pipe 166. Periodically the filter is backwashed to the vegetation cell or first treatment tank by closing valve 164 and opening valves 167,168.

Second Preferred Embodiment

Figure 9:
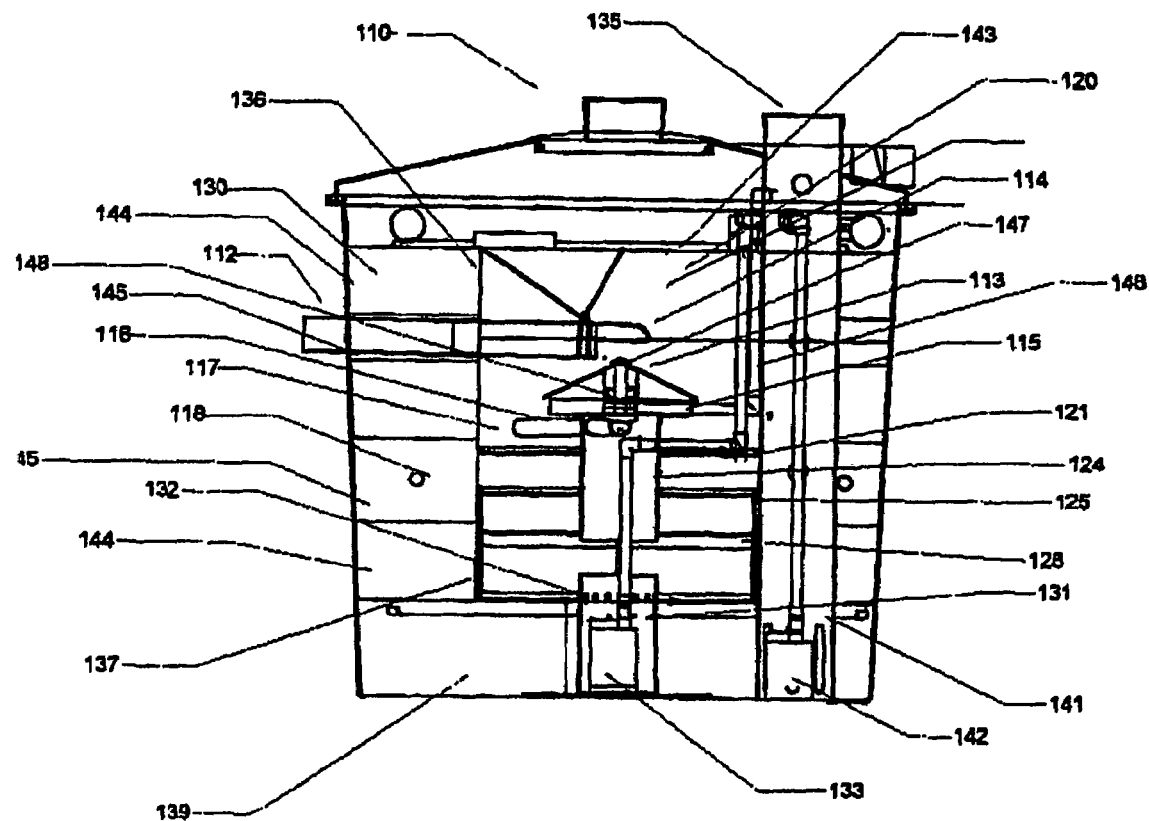
FIG. 9 is a vertical cross-sectional view of a second embodiment of the waste treatment apparatus according to the present invention.
Figure 10:
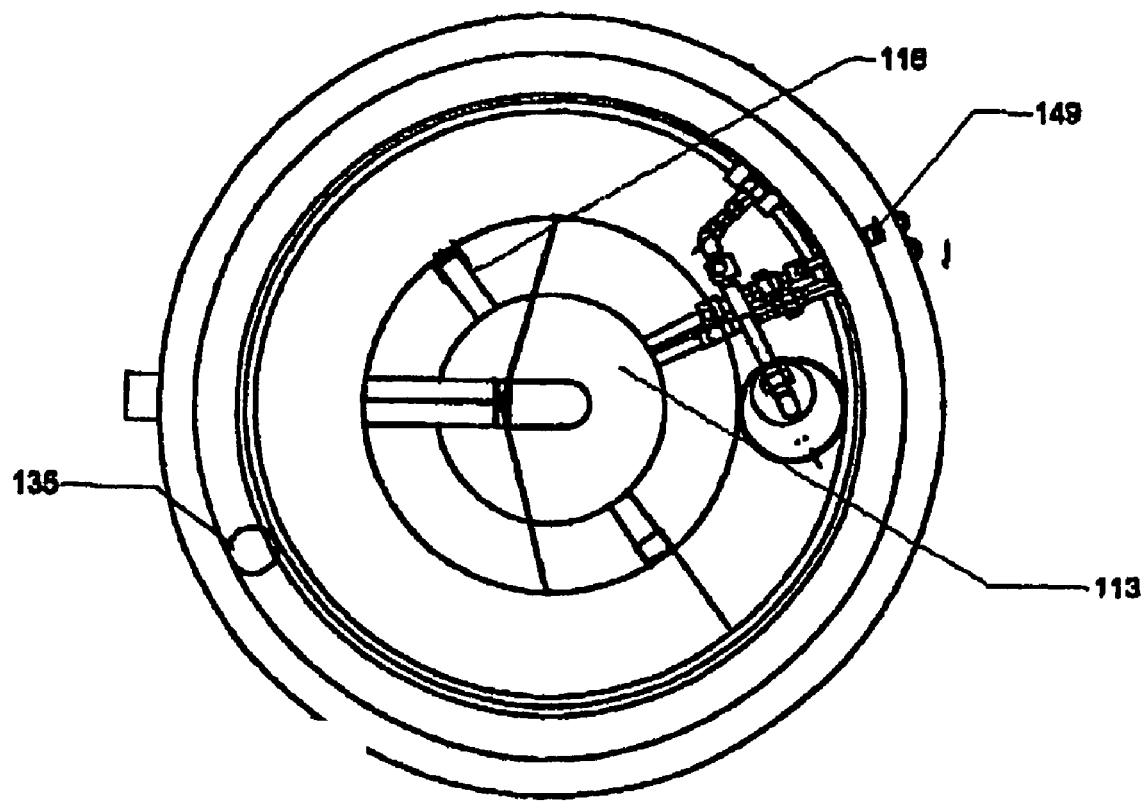
FIG. 10 is an upper horizontal cross sectional view of the apparatus of FIG. 9.
Figure 11:
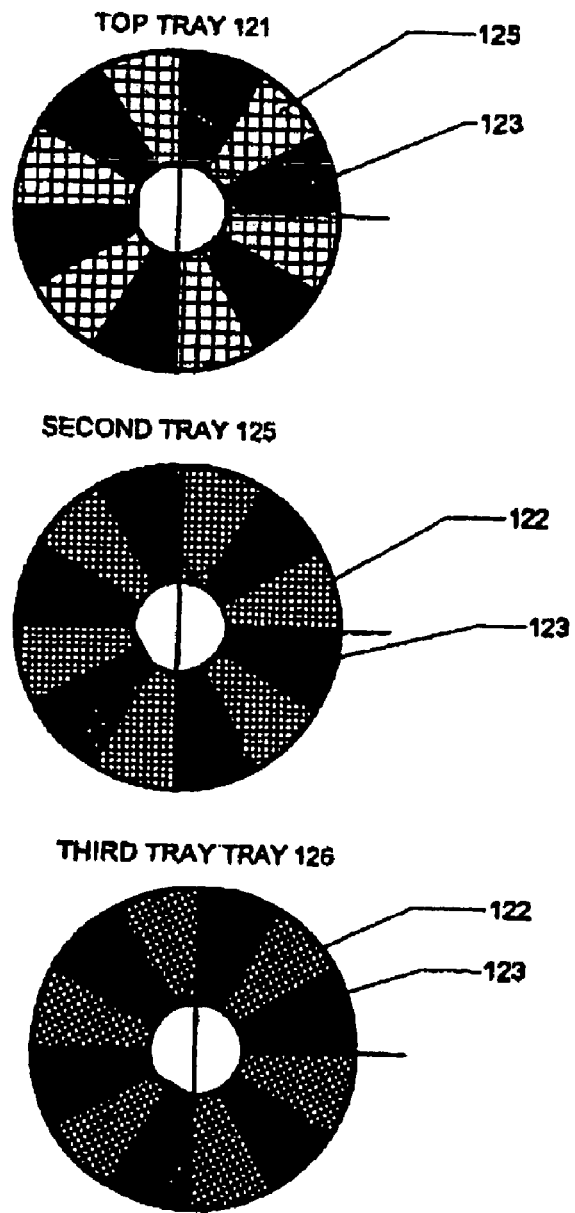
FIG. 11 is a plan view of the support screens of the apparatus of FIG. 9.

With reference to FIGS. 9 to 11, there is shown a waste treatment apparatus 110 which can be installed either above or below ground level. The apparatus 110 is aerated through a number of vents 135.

The apparatus 110 consists of a first treatment chamber 111. Liquid and solid waste enters the chamber 111 through waste pipe 112. The outlet of the pipe 112 is positioned above a separation cone 113. The end of the pipe 112 has a flexible geotextile skirt 114 which serves to dampen the rush of the waste stream onto the cone 113.

The cone 113 is formed from a porous woven mesh membrane that allows at least a proportion of the liquid in the waste stream to pass through. The cone 113 allows about 95% of the liquid in the waste stream to separate from the solid waste.

The liquid from the cone 113 collects in a tray 115 and then drains through two exit pipes 116 arranged 180° apart into respective funnels 117. The liquid is then distributed by pipe 118 into a series of layered trickle beds 130. The liquid is distributed into the beds 130 by pipes 118.

The majority of the solid waste in the inlet stream and a relatively small quantity of liquid is deflected by separating cone 113 outwardly before falling downwardly onto top tray 121. The top tray 121 is comprised of alternating regions of relatively coarse mesh 122 (25 mm gaps) and relatively fine mesh 123 (e. g. shadecloth).

Worms, other living organisms, wormcast and fibre mix are introduced into the centre chamber 124 prior to commissioning of the apparatus 110. The worms and other living organisms can move through the porous wall of the centre chamber 124 to the waste caught on the tray 121.

Smaller material and decomposed larger material falls through the top tray 121 onto the middle tray 125 below where it again is consumed by the worms and other living organisms that have moved out of chamber 124. The middle tray 125 also has alternating regions of coarse mesh 122 (13 mm gaps) and fine mesh 123.

The regions of fine mesh 123 of middle tray 125 are offset such that the fine mesh 123 of the middle tray 125 is positioned below the coarse mesh regions 122 of top tray 121. In this way, any solid material that falls straight through top tray 121 is caught by the middle tray 125.

As the material on the middle tray 125 breaks down it falls to a third bottom tray 126 where it again can be consumed by the worms and other living organisms that have moved out of chamber 124. Bottom tray 126 again has regions of relatively coarse mesh 122 (5 mm gaps) and fine mesh 123 (e. g. shade cloth). The fine mesh 123 of the bottom tray 126 is again offset from that of the middle tray 125 such that matter that falls through the mesh 122 of the middle tray 125 preferably lands on the fine mesh 123 of bottom tray 126.

Once the material falls through bottom tray 126 it builds up on a bed of fine fibre 127 supported on a membrane 128 and drainage cells 129 that are positioned during start-up.

As the solids build up on bed 127 they fall into the centre well 131. Some liquid also flows into this well 131 either with the solids or through drainage holes 132 from drainage cells 129. Pump 133 in well 131 is activated when the liquid reaches a pre-determined height. The solids and the liquid in well 131 are then pumped to an annular distribution pipe 134 and pass through small holes into a collection tube consisting of agricultural pipe covered by filter sock. The solids are retained in the tube for removal during a service of the apparatus and the liquid passes through the sock into the top of the trickle beds 130. Alternatively the liquid and solids can be pumped to a vegetation cell as in the first embodiment.

The trickle beds 130 are separated from the first treatment zone 120 by a wire screen and porous shade cloth membrane 136 in the upper section of the chamber 111 and by an impervious membrane 137 at the base of the chamber 111.

Aerobic bacteria form within the trickle beds 130 and serve to reduce the BOD and nitrogen in the wastewater as it passes through the beds 130.

The liquid leaving the trickle beds 130 passes into the collection chamber 139.

The liquid from the collection chamber 139 flows into pump well 141 where it is pumped by pump 142 out of the chamber 139. The liquid can be recirculated back through the trickle beds 130, pumped to a granular filter of a further liquid treatment apparatus 160, or used for cleaning the separation cone 113.

The liquid is recirculated to the trickle beds 130 through annularly disposed, distribution nozzles 143. The frequency of recirculation is set by a controller to maximise BOD reduction in the trickle beds 130. The recirculation continues either until a low level float probe in well 141 is activated or the recirculation time set in the controller is exceeded. The liquid passes down through the beds 130 which comprises a alternate layers of fine media 144, such as peat moss, followed by course media 145, such as chopped up 63 mm agricultural pipe. Each layer of the course media 145 is ventilated through holes in vent pipe 135.

Liquid passing through the separation cone 113 and entering the trickle beds 130 through distribution pipe 118 passes through at least one layer of fine trickle media 144 and one layer of course media 145 before it enters collection chamber 139.

At preset intervals, for example 1 minute per day, the controller can open a valve and a preset quantity of treated water can be pumped to the cone 113 through pipe 146 to clean any accumulated solids off the membrane 113. The liquid is directed tangentially across the membrane 113 through a slit around the circumference of nozzle device 147 and also up through the screen through nozzles 148. The washing time is set prior to pump out to ensure there is always water available for cleaning.

The apparatus can include a high level probe, connected to a visual alarm with buzzer positioned within the house, to signal a malfunction of the system and to ensure manual override of the pump 142 when required.

At preset times or when the high level probe is activated, the liquid in the collection chamber 139 can be pumped through pipe 149 to a trench or further liquid treatment apparatus.

Separator

FIG. 1 shows one preferred form of the separator ("separating means") of the present invention. Referring to FIG. 1, there is shown a separating means substantially in the shape of a cone 14, having an inclined surface 25 and a curved lower surface 26

Figure 12:
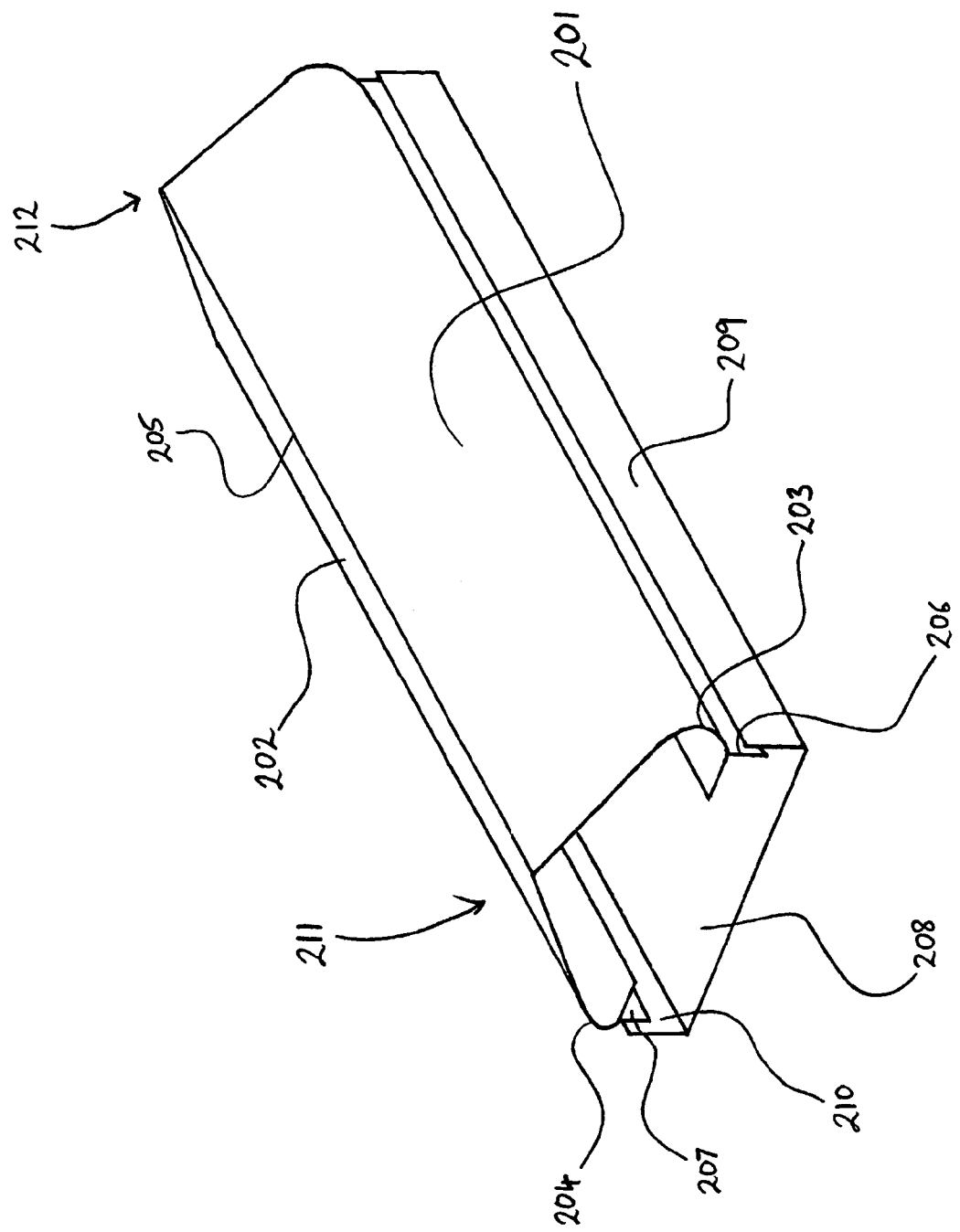
FIG. 12 is a perspective view of a separating means according to the present invention.

FIGS. 12 and 13 show another preferred form of the separating means of the present invention. Referring to FIG. 12, there is shown a separating means having two substantially non porous inclined surfaces 201 and 202, each surface having corresponding curved lower outer longitudinal edges 203 and 204 respectively. The surfaces 201 and 202 are generally elongate and share a common longitudinal upper edge, which defines a substantially horizontal top edge 205 of the separating means. Each of the curved lower outer edges 203 and 204 has a corresponding longitudinal flange 206 and 207 respectively. The longitudinal flanges are positioned for directing liquid waste into a liquid collection means. The liquid collection means is generally in the form of a tray 208 positioned beneath the separating means. The side walls 209 and 210 of the tray 208 are positioned outside the longitudinal flanges 206 and 207 so that separated liquid drips into the tray 208.

The separating means has a first end 211 and a second end 212. In use, the first end is located adjacent to a waste discharge outlet (not shown), and the second end is located distal to the waste discharge outlet. Hence, in use, waste is delivered longitudinally along the top edge 205 of the separating means.

Referring to FIGS. 13(a) and (b), the separating means is tapered towards the second end 212 of the separating means, such that the second end 212 is smaller in cross-section that than the first end 211.

Advantages

The advantages of the present invention include the decomposition of domestic waste onsite through the passive separation of liquid and solid waste and identification and use of suitable treatments for each substrate. With the preferred embodiment of the invention there is no requirement to remove bi-products from the treatment site. The water quality produced from the treatment system is relatively high compared with other primary treatment systems. Therefore the water discharged from the treatment system requires fewer steps to produce relatively high quality water.

Furthermore the separation and respective treatments for the liquid and solid wastes is arranged in a compact manner that minimizes capital and installation cost and allows scaling up of the treatment system and or the use of multiple treatment system modules.

There is also the provision of reusable water and treated solids waste as nutrient plant media.

As the waste is largely aerobically digested, the treatment system has the further advantage that little if any unpleasant odours are produced during decomposition.

Variations

It will of course be realised that while the foregoing has been given by way of illustrative example of this invention, all such and other modifications and variations thereto as would be apparent to persons skilled in the art are deemed to fall within the broad scope and ambit of this invention as is herein set forth.

Throughout the description and claims this specification the word "comprise" and variations of that word such as "comprises" and"comprising", are not intended to exclude other additives, components, integers or steps.

What is claimed is:

1. A separator adapted for separating liquid and solid waste, having a substantially non porous inclined surface with a curved lower outer edge to allow solid waste to thereoff fall while liquid waste moves around the curved lower outer edge.

2. The separator according to claim 1, having a height dimension of less than about 200 mm.

3. The separator as claimed in claim 1, comprising a plurality of substantially non porous inclined surfaces.

4. The separator as claimed in claim 1, wherein the surface is substantially in the shape of a cone with the apex locatable adjacent a waste discharge outlet, the surface includes a base surface, and the curved lower edge and base surface locatable to overhang a liquid collection means.

5. The separator as claimed in claim 1, wherein the curved lower outer edge includes a flange positioned for directing liquid waste into a liquid collection means.

6. The separator as claimed in claim 5, wherein said flange extends downwardly from a substantially horizontal part of the curved lower outer edge.

7. The separator as claimed in claim 1, wherein the inclined surface is an inclined wall that has a convex curved lower edge.

8. The separator as claimed in claim 7, wherein the convex curved lower edge extends, at least in part, substantially horizontally under the inclined wall.

9. The separator as claimed in claim 1, comprising two substantially non porous inclined surfaces, each having curved lower outer edges, and sharing a common upper edge which defines an apical top edge.

10. The separator as claimed in claim 9, further comprising a longitudinal flange along each of the curved lower outer edges, said longitudinal flanges being positioned for directing liquid waste into a liquid collection means.

11. The separator as claimed in claim 9, wherein each of the inclined surfaces is elongate and shares a common longitudinal edge.

12. The separator as claimed in claim 9, wherein a first end of the separator is locatable adjacent to a waste discharge outlet and second end of the separator is locatable distal to the waste discharge outlet.

13. The separator as claimed in claim 12, wherein each of the inclined surfaces is tapered towards the second end of the separator, such that the second end is smaller in cross-section than the first end.

14. The separator as claimed in claim 12, wherein, in use, waste is delivered longitudinally along the top edge of the separator.

15. A waste treatment system including a decomposition chamber having an inlet, said decomposition chamber comprising:
a separator, as claimed in any one of the claims 1 to 2; and
a solid waste treatment means and a liquid waste treatment means.

16. A waste treatment system as claimed in claim 15, wherein the separator, solid waste treatment means and liquid waste treatment means are arranged in relative close proximity with each other to provide a compact treatment apparatus.

17. A waste treatment system as claimed in claim 15, wherein the decomposition chamber is circular in cross section to provide maximum usage of space within the chamber and house the components in a compact manner.

18. A waste treatment system as claimed in claim 15, wherein the waste treatment system is modular with a plurality of units arranged to handle larger amounts of waste.

19. A waste treatment system as claimed in claim 15, including a liquid collection chamber for collecting liquid waste from the separator and introducing said liquid waste to the liquid waste treatment means.

20. A waste treatment system as claimed in claim 15, further including a vegetation cell for supporting a plant, wherein, in use, at least one of treated solid waste and treated liquid waste is discharged to the vegetation cell.

21. A waste treatment system as claimed in claim 15, wherein the separator is in the form of either:
(a) a substantially non-porous separating cone, wherein an apex of said cone is located adjacent a waste discharge outlet; or
(b) two elongate substantially non porous inclined surfaces, each having curved lower outer longitudinal edges, and sharing a common upper longitudinal edge which defines a substantially horizontal top edge of the separator, wherein one end of the separator is located adjacent a waste discharge outlet.

22. A waste treatment system as claimed in claim 19, wherein at least one of the inlet and the waste discharge outlet includes at least one of a skirt and a baffle for restricting flow.

23. A waste treatment system as claimed in claim 15, including one or more substantially horizontal support mesh screens, said mesh screens being positioned for receiving solid waste below the separator.

24. A waste treatment system as claimed in claim 23, including a plurality of support mesh screens with an upper screen having comparatively wider apertures than a lower adjacent screen.

25. A waste treatment system as claimed in claim 23, wherein particulate solids can accumulate in the pump well and are then pumped out at regular intervals or when a predetermined height is reached.

26. A waste treatment system as claimed in claim 23, wherein the mesh screens support worms and other suitable organisms for decomposing waste and/or reducing particle size.

27. A waste treatment system as claimed in claim 23, wherein a lowermost mesh screen is inclined to direct decomposed particulate solids towards a solids pump well.

28. A waste treatment system as claimed in claim 23, wherein an uppermost mesh screen includes a plurality of baffles for breaking up the solid waste.

29. A waste treatment system as claimed in claim 28, wherein the baffles are in the form of mushroom-shaped projections or in the form of nodules.

30. A waste treatment system as claimed in claim 15, wherein the liquid waste treatment means includes one or more layers of trickle bed media.

31. A waste treatment system as claimed in claim 30, wherein the liquid waste treatment means includes a plurality of layers with alternating relatively coarse trickle bed media and relatively fine trickle bed media.

32. A waste treatment system as claimed in claim 31, wherein each of the relatively coarse trickle bed media layers is well ventilated.

33. A waste treatment system as claimed in claim 30, wherein the trickle bed layers are formed annularly about the solid waste treatment means.

34. A waste treatment system as claimed in claim 30, wherein a wall between the trickle bed layers and the solid waste treatment means is porous for allowing ventilation of the trickle bed layers and a passage for worms and suitable organisms.

35. A waste treatment system as claimed in claim 30, including a liquid pump well for collecting liquid that has passed through the trickle bed.

36. A waste treatment system as claimed in claim 35, wherein the liquid pump well includes a pump for pumping liquid out of the liquid pump well at regular intervals or when the liquid reaches a predetermined level.

37. A waste treatment system as claimed in claim 36, wherein liquid in the liquid pump well may be reintroduced to the trickle bed or discharged from the treatment apparatus.

38. A waste treatment system as claimed in claim 36, wherein the collected liquid may pass into the solids pump well for removal when the pump in the liquid pump well fails.

39. A waste treatment system as claimed in claim 15, wherein accumulated particulate solids can pass through to the liquid pump well for removal when the solid pump fails.

40. A waste treatment system as claimed in claim 39, wherein at least one of the solid waste treatment means and the liquid waste treatment means includes a vegetation cell to supply at least one of nutrients and moisture to a plant-growing medium.

41. A self-contained waste treatment system, which does not require human intervention for removal of treated waste, comprising:

a decomposition chamber having a waste chamber inlet, said decomposition chamber housing a separator, a solid waste treatment means and a liquid waste treatment means, the separator including a substantially non porous inclined surface with a curved lower outer edge to allow solid waste to fall off the separator while liquid waste moves around the curved lower outer edge; and a vegetation cell for supporting a plant, wherein, in use, treated solid waste and, optionally, treated liquid waste is discharged to the vegetation cell.

42. A self-contained process for treating waste, which does not require human intervention for removal of treated waste, said process comprising:

separating liquid and solid waste using a separator by having solid and liquid waste travel down an inclined, substantially non porous surface, allowing solid waste to fall off a lower edge of the surface, and having liquid waste travel around a lower curved edge of the surface;

treating the separated liquid waste in a liquid waste treatment means;

treating the separated solid waste in a solid waste treatment means;

optionally further treating the liquid waste; and discharging the treated solid waste and, optionally, the treated liquid waste to a vegetation cell.

* * * * *

UNITED STATES PATENT AND TRADEMARK OFFICE
CERTIFICATE OF CORRECTION

PATENT NO. : 6,991,728 B2
DATED : January 31, 2006
INVENTOR(S) : Ames et al.

It is certified that error appears in the above-identified patent and that said Letters Patent is hereby corrected as shown below:

Column 13,
Line 16, delete "thereoff fall" and insert -- fall thereoff --.

Column 14,
Line 32, delete "claim 19," and insert -- claim 21, --.

Signed and Sealed this

Second Day of May, 2006

JON W. DUDAS
*Director of the United States Patent and Trademark Office*